United States Patent [19]

Harding

[11] 4,423,522
[45] Dec. 27, 1983

[54] DEVICE FOR THE IMAGING OF BODY LAYERS BY MEANS OF MONOENERGIC RADIATION

[75] Inventor: Geoffrey Harding, Halstenbek, Fed. Rep. of Germany

[73] Assignee: U.S. Philips Corporation, New York, N.Y.

[21] Appl. No.: 273,547

[22] Filed: Jun. 15, 1981

[30] Foreign Application Priority Data

Jun. 21, 1980 [DE] Fed. Rep. of Germany ....... 3023263

[51] Int. Cl.³ ............................................. G01N 23/20
[52] U.S. Cl. ............................................ 378/87; 378/6
[58] Field of Search ...................................... 378/87, 6

[56] References Cited

U.S. PATENT DOCUMENTS 4,229,651 10/1980 Danos .................................... 378/87
4,258,256 3/1981 Harding .................................. 378/87

Primary Examiner—Craig E. Church
Attorney, Agent, or Firm—Jack E. Haken

[57] ABSTRACT

A scatter radiation device for determining the internal structure of a body comprises a monoenergic radiation source for emitting a narrow primary beam which penetrates the body, at least one slit diaphragm device which is situated outside the primary beam and which comprises a plurality of slit diaphragm apertures which extend approximately perpendicularly to the primary beam, and a detector device which extends transversely of the longitudinal slit direction and which comprises separate detectors which receive scatter radiation produced in the body by the primary beam. The scatter radiation which each time originates from a point of the primary beam and which passes through all slit diaphragm apertures, is measured by different detectors of the detector device, and thus serves for determining the body density at the corresponding point.

4 Claims, 3 Drawing Figures

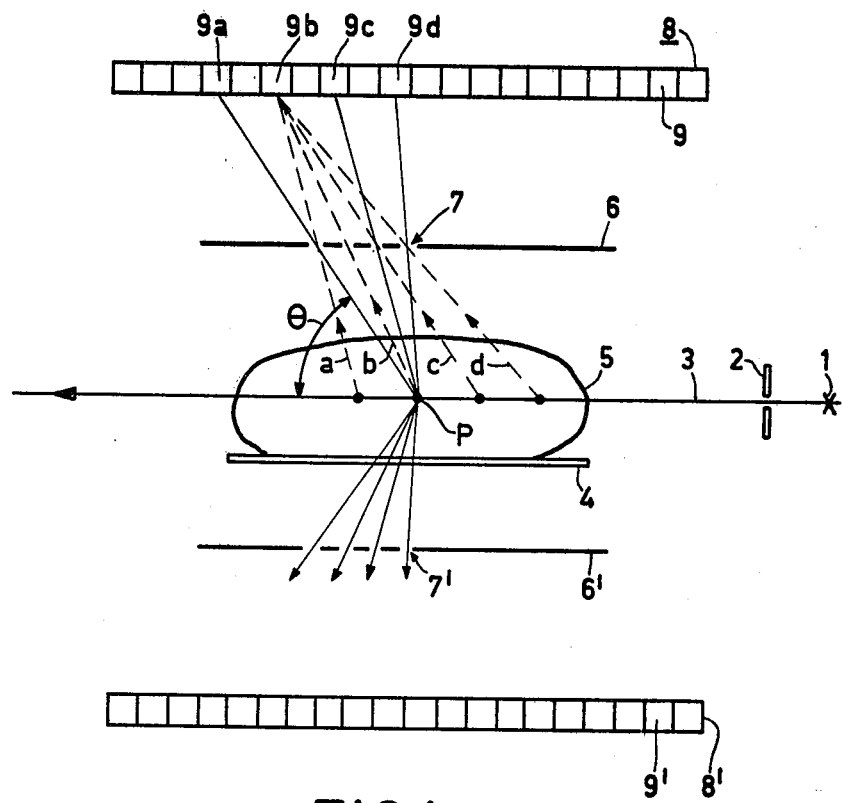
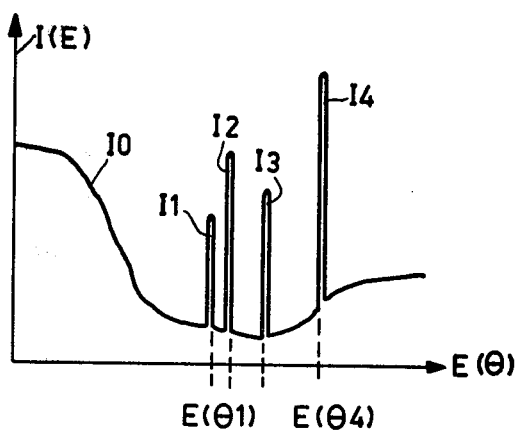
FIG.1
FIG.2

DEVICE FOR THE IMAGING OF BODY LAYERS BY MEANS OF MONOENERGIC RADIATION

The invention relates to a device for determining the internal structure of a body, comprising at least one radiation source for generating a narrow monoenergic primary beam which penetrates the body, at least one slit diaphragm device which is arranged adjacent the path of the primary beam with a longitudinal slit direction of which extends in a direction transverse to of the primary beam, a detector device which extends transverse to the longitudinal slit direction and which comprises separate detectors for the detection of scatter radiation which is produced in the body by the primary beam and which passes through the slit, an electronic device for the processing of detector signals, and a display device for processed scatter signals.

A device of this kind is known from German Offenlegungsschrift No. 27 13 581. This device enables the determination of density distributions, for example, the electron density distribution, in a layer of a body. A body to be examined is then irradiated, for example, by means of a narrow monoenergic gamma beam. Scatter radiation produced in the body in the path of the primary beam reaches a row of detectors via a slit diaphragm arranged adjacent the path of the primary beam, the slit diaphragm and the detectors being positioned so that each detector can intercept only a spatially limited part of the scatter radiation produced by the primary beam. Detector output signals thus are a qualitative representation of the density distribution in the body along the primry beam. The body can subsequently be displaced over a distance corresponding to approximately the width of the primary beam, perpendicularly to the direction thereof, to enable linewise scanning of the body. It is also possible to arrange such a slit diaphragm device or detector device on both sides of the primary beam in order to increase the scatter radiation to be measured.

The number of scatter photons incident on a detector via the slit diaphragm, however, is comparatively small, because the width of the slit diaphragm must be small in order to obtain adequate spatial resolution of the system. Therefore, in order to obtain good quality images of body layers, the body to be examined is irradiated with a comparatively high radiation dose.

It is an object of the invention to provide a device for determining the internal structure of a body which allows the body to be irradiated with a smaller dose, without the image quality of the body layer images being affected thereby.

This object in accordance with the invention is achieved in that the slit diaphragm comprises several slit diaphragm apertures which are adjacently arranged in parallel, detector elements supplying energy-dependent detector output signals are connected to an electronic circuit for energy discrimination of the detector output signals in order to form scatter signals from the detector output signals per radiation energy. The electronic circuit are connected to a selection circuit in order to select from the scatter signals of all detectors those signals whose scatter radiation originates from the same part of the body which is activated by the primary beam. The selection circuit is connected to an electronic processing device for determination and display of the internal body structure by means of the selected scatter signals.

Thanks to the increased number of slit diaphragm apertures, the sensitivity of such a device is substantially increased for the same spatial resolution of the system, because the aperture area of the diaphragm device is increased according to the number of M slit diaphragm apertures with respect to the known slit diaphragm. Therefore, for example, body layer images can be obtained with the same signal-to-noise ratio as in the known device, but with a radiation dose which is M times smaller. Alternatively, with the same radiation dose body layer images of higher quality can be obtained.

The drawing shows an embodiment in accordance with the invention.

FIG. 1 is a sectional view of a diagnostic apparatus comprising a slit diaphragm device comprising several slit diaphragm apertures.

FIG. 2 shows the radiation intensity incident on a detector in dependence of the energy thereof.

Figure 3:
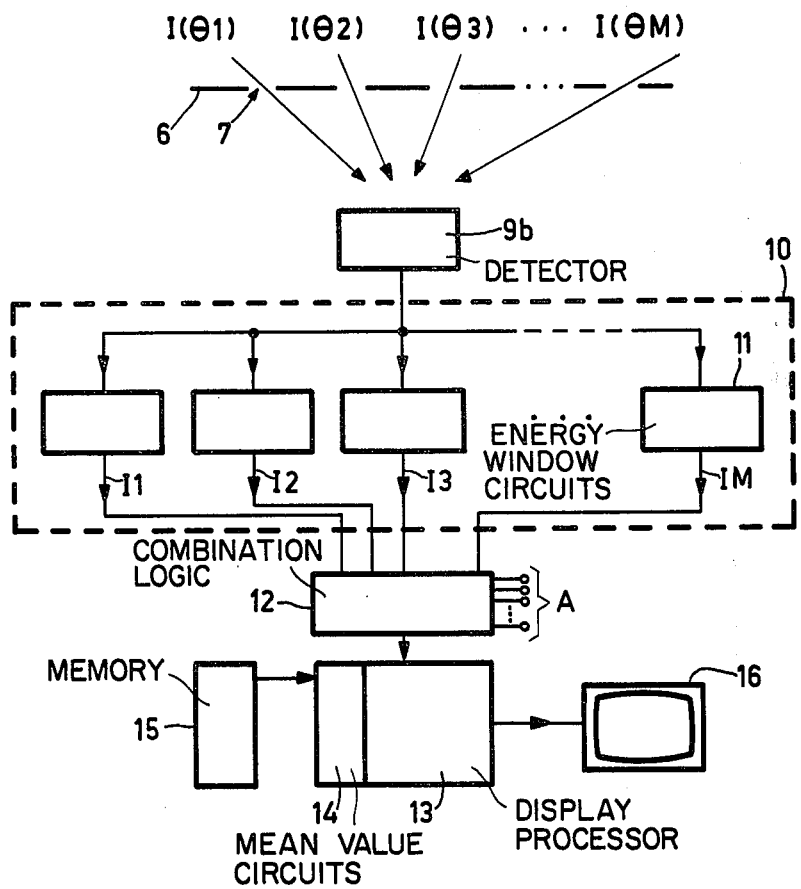
FIG. 3 shows a block diagram for the processing of the output signals of a detector.

FIG. 1 is a sectional view of a diagnostic apparatus in accordance with the invention. The apparatus comprises a monoenergic radiation source 1, for example, 137 Cs at 662 KeV, whose radiation is stopped down by a diaphragm 2 in order to form a narrow primary beam 3 which irradiates a body 5 arranged on a table 4. The scatter radiation produced in the part of the body 5 irradiated by the primary beam 3 reaches detector groups 8 and 8' via a diaphragm devices 6 and 6' which comprises several parallel adjacently arranged slit diaphragm apertures 7 and 7' which extend perpendicular to the primary beam 3 and which are preferably displaceable in the width direction thereof. Detector groups 8, 8' is composed of a rather large number of separate detectors 9, 9' which are adjacently situated, for example, parallel to the primary beam 3. The detectors 9, 9' may be strip-shaped and arranged so that their principal dimension extends perpendicularly to the primary beam 3 and parallel to the longitudinal direction of the slit diaphragm apertures 7, 7'. The body 5 is arranged to be displaceable with respect to the diagnostic apparatus in order to enable scanning of different parts of the body.

When the energy of the radiation of the radiation source 1 has the value $E_o$, the energy E ($\theta$) of radiation scattered in the body at the angle $\theta$ with rspect to the primary radiation direction can be expressed in general as:

$$e(\theta) = \frac{E_o \cdot m_e c^2}{m_e c^2 + E_0(1 - \cos\theta)} \quad (1)$$

in which $m_e$ is the electron mass and c is the velocity of light. Using the diaphragm device which is situated between the body and the detector device several scatter radiation paths, for example, four scatter radiation paths a–d in FIG. 1, are collimated for a detector 9b, said paths extending at different angles $\theta$ with respect to the primary beam. As a result, the scatter radiation following each of paths a–d has a different energy E($\theta$) which is determined in accordance with formula (1). The energy spectrum of the radiation $I=f(E)$ measured by the detector 9b then corresponds to the distribution shown in FIG. 2. Radiation with the energy E($\theta$4) follows the scatter path d in FIG. 1 (scatter signal I4), while radiation with the energy E($\theta$1) follows the path a (scatter signal I1). The reference IO denotes the radiation background which is formed inter alia by the incomplete energy conversion of the scatter radiation in the detector $9b$ into a corresponding detector output signal, by multiple scattering and by detector noise. If this radiation background is correctly subtracted from the scatter signals I1 ... I4, the scatter radiation intensity which actually reaches a detector (for example, the detector $9b$) and which passes through a slit diaphragm aperture 7, 7' can be determined. To this end, the detectors 9, 9' must have a comparatively high energy resolution. For example, if use is made of cooled Ge/Li semiconductor detectors, the diaphragm device 6, 6' may comprise approximately 20 slit diaphragm apertures 7, 7' when 137 Cs is used as the radiation source.

If such an energy spectrum $I=f(E)$ is known from each of the detectors 9, 9', the internal structure of the body 5 (for example, the electron density of the body 5 along the primary beam 3) along the primary beam 3 can be determined therefrom. For example, for the point P in FIG. 1 this is realized by means of a selection circuit 12 (FIG. 3) so that from the energy spectrums of the detectors $9a$–$d$ those scatter signals are selected whose scatter radiation originates from the common point P. This is readily possible because the point P can be unambiguously determined in a fixed geometrical arrangement of the detectors 9, 9' relative to the diaphragm device 6, 6' and the primary beam 3, by way of the energic position of the scatter signals in the relevant spectrums. The selected scatter signals which relate to the point P are then further processed in that, for example, the attenuation of the primry beam 3 in the body 5 and the attenuation of the scatter radiation along the scatter radiation paths a–d is taken into account; this is already known from German Offenlegungsschrift No. 27 13 581. Subsequently, a mean value is formed of the scatter signals or the electron densities obtained from the scatter signals thus processed, for example, a weighted mean value.

FIG. 3 shows a block diagram for the processing of the detector output signals. A detector, for example, the detector $9b$, is each time connected to an electronic circuit 10 which sorts the detector output signals in accordance with the energy of the scatter radiation $I(\theta)$; ... $I(\theta M)$ passing through the M slit diaphragm apertures 7 and which forms scatter signals I1 ... IM from the detector output signals each time associated with a scatter radiation energy. The electronic circuit 10 may comprise circuits 11 which form M energy windows and which supply an output signal only if the input signal (detector output signal) is within a given range of values which corresponds to a predetermined energy range of the scatter radiation. The output signals of the circuits 11 associated with each energy range are then summed in order to form the scatter signals I1 ... IM. This operation can also be performed by means of the electronic circuit 10.

The electronic circuits 10 of all detectors 9, 9' themselves are connected to a common selection circuit 12 whereto only one circuit 10 is connected in FIG. 3 for the sake of clarity. All other circuits 10 are similarly connected to the inputs A of the selection circuit 12, which itself selects from the scatter signals associated with all detectors 9, 9' those signals whose radiation energy originates from the same body zone P which is activated by the primary beam 3.

The selection circuit 12 is also connected to an electronic processing device 13 which performs the correction of the selected scatter signals as regards the attenuation of the primary beam 3 and the scatter radiation along the scatter beam paths a–d in the body 5. Also provided is a mean value former 14 for forming the mean value of the electron densities formed from the scatter signals thus processed. The mean value former 14 may be connected to a memory 15 for the storage of weighting factors for the formation of a weighted mean value. A monitor 16 for the display of the mean values formed or the structure distribution of the body is connected to the processing device 13.

What is claimed is:

1. A device for determining the internal structure of a body, comprising:
   radiation source means which generate a narrow monoenergic primary beam of radiation which penetrates the body;
   diaphragm means disposed adjacent the path of the primary beam which define a plurality of adjacent, parallel, longitudinal slits which extend in a direction transverse to the primary beam;
   detector means which extend transverse to the direction of the slits and which comprise a plurality of separate detectors which detect scatter radiation, which radiation is produced in the body by the primary beam and has passed through the slits, and which produce energy-dependent detector signals in response thereto;
   energy discrimination means which process the detector signals from each detector to produce separate discriminator output signals for each of a plurality of scatter radiation energies detected thereby;
   selector means which sum signals in preselected groups of the discriminator output signals each group being selected to contain signals produced by scatter radiation which originates in a separate region of the primary radiation beam; and
   means which display the summed signals as a representation of the internal body structure.

2. The device of claim 1 wherein the selector means includes means which form the mean value of selected scatter signals.

3. A device as claimed in claim 1 or 2 wherein the detectors are strip-shaped and have a principal dimension which is disposed parallel to the longitudinal direction of the slits.

4. A device as claimed in claim 1 wherein the detector means comprise semiconductor detectors.

* * * * *